(12) United States Patent
Chou et al.

(10) Patent No.: US 11,389,104 B2
(45) Date of Patent: Jul. 19, 2022

(54) SYSTEM OF JOINT BRAIN TUMOR AND CORTEX RECONSTRUCTION

(71) Applicant: SONY GROUP CORPORATION, Tokyo (JP)

(72) Inventors: Chen-Rui Chou, San Jose, CA (US); Bi Song, San Jose, CA (US); Ming-Chang Liu, San Jose, CA (US)

(73) Assignee: SONY GROUP CORPORATION, Tokyo (JP)

( * ) Notice: Subject to any disclaimer, the term of this patent is extended or adjusted under 35 U.S.C. 154(b) by 1261 days.

(21) Appl. No.: 15/207,353

(22) Filed: Jul. 11, 2016

(65) Prior Publication Data

US 2018/0008187 A1    Jan. 11, 2018

(51) Int. Cl.
| | |
|---|---|
| A61B 5/00 | (2006.01) |
| A61B 5/055 | (2006.01) |
| G06T 7/00 | (2017.01) |
| G06K 9/62 | (2022.01) |
| G01R 33/56 | (2006.01) |
| G06T 7/11 | (2017.01) |
| G06T 7/162 | (2017.01) |
| G01R 33/50 | (2006.01) |

(52) U.S. Cl.
CPC .......... *A61B 5/4064* (2013.01); *A61B 5/0035* (2013.01); *A61B 5/0042* (2013.01); *A61B 5/055* (2013.01); *A61B 5/7267* (2013.01); *G01R 33/5608* (2013.01); *G06K 9/6262* (2013.01); *G06K 9/6282* (2013.01); *G06T 7/0014* (2013.01); *G06T 7/11* (2017.01); *G06T 7/162* (2017.01); *A61B 2576/026* (2013.01); *G01R 33/50* (2013.01); *G06T 2207/10088* (2013.01); *G06T 2207/20081* (2013.01); *G06T 2207/20112* (2013.01); *G06T 2207/30016* (2013.01); *G06T 2207/30096* (2013.01); *G06V 2201/03* (2022.01)

(58) Field of Classification Search
CPC .................................................... A61B 5/0042
See application file for complete search history.

(56) References Cited

U.S. PATENT DOCUMENTS

| | | |
|---|---|---|
| 6,591,004 B1 | 7/2003 | VanEssen et al. |
| 8,023,734 B2 * | 9/2011 | Jolly .................... G06T 7/12 382/171 |
| 9,547,908 B1 * | 1/2017 | Kim .................. G06K 9/00362 |

(Continued)

FOREIGN PATENT DOCUMENTS

WO    2016007518 A1    1/2016

*Primary Examiner* — Rochelle D Turchen
(74) *Attorney, Agent, or Firm* — O'Banion & Ritchey LLP; John P. O'Banion

(57) ABSTRACT

System for performing fully automatic brain tumor and tumor-aware cortex reconstructions upon receiving multi-modal MRI data (T1, T1c, T2, T2-Flair). The system outputs imaging which delineates distinctions between tumors (including tumor edema, and tumor active core), from white matter and gray matter surfaces. In cases where existing MRI model data is insufficient then the model is trained on-the-fly for tumor segmentation and classification. A tumor-aware cortex segmentation that is adaptive to the presence of the tumor is performed using labels, from which the system reconstructs and visualizes both tumor and cortical surfaces for diagnostic and surgical guidance. The technology has been validated using a publicly-available challenge dataset.

20 Claims, 12 Drawing Sheets

(56) References Cited

U.S. PATENT DOCUMENTS

| | | | |
|---|---|---|---|
| 2006/0193917 A1* | 8/2006 | Matthews | A61P 35/00 |
| | | | 424/486 |
| 2008/0075348 A1* | 3/2008 | Rappaport | G06K 9/6255 |
| | | | 382/132 |
| 2008/0144907 A1 | 6/2008 | Shen | |
| 2010/0260396 A1* | 10/2010 | Brandt | G06K 9/4671 |
| | | | 382/131 |
| 2013/0163836 A1* | 6/2013 | Pau | G06T 7/00 |
| | | | 382/128 |
| 2013/0324841 A1* | 12/2013 | Kamen | A61B 8/0841 |
| | | | 600/424 |
| 2016/0005183 A1 | 1/2016 | Thiagarajan et al. | |
| 2016/0035093 A1 | 2/2016 | Kateb et al. | |
| 2016/0203263 A1* | 7/2016 | Maier | G06F 19/321 |
| | | | 705/2 |
| 2018/0325461 A1* | 11/2018 | Carroll | A61B 5/055 |

* cited by examiner

SYSTEM OF JOINT BRAIN TUMOR AND CORTEX RECONSTRUCTION

CROSS-REFERENCE TO RELATED APPLICATIONS

Not Applicable

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

The technology of this disclosure pertains generally to analyzing magnetic resonance image (MRI) data for detecting and reconstructing imaging of tumors, and more particularly to a fully automatic brain tumor and tumor-aware cortex reconstruction system which provides enhanced segmentation and training.

2. Background Discussion

In preparations and during neurosurgery, surgeons need to fully understand the exact location of the tumor and its relationship to the critical cortical structures like White matter and Gray matter. Typically, this process requires several hours of a clinicians' time to manually contour the tumor and white matter and gray matter boundaries from multiple pre-operative MRI scans.

As manual processing is so labor intensive, automated approaches are being sought. Yet, analyzing magnetic resonance image (MRI) data for the detection, reconstruction and imaging of tumors is a complex and difficult process. Existing automated systems for analyzing this data have proven to have a number of shortcomings. For example, systems typically fail to take into account deformed anatomy which arises in response to a tumor. In addition, many automated approaches can distort the reconstruction, such as by overcompensation. Furthermore, the use of available low resolution datasets (e.g., BraTS2105) limits discernment and imaging capabilities.

One important refinement in existing MRI detection and reconstruction was the segmenting of the cerebrum to separate the cerebrum and cerebellum from blurry and deformed boundaries. In this process, brain MRI data was processed to extract the brain and identify the gray matter and white matter, then the cerebrum segmented out, after which a reconstruction was performed of the structural surfaces of the cerebrum. This process involved the use of graph cuts with seeds on the mid-sagittal plan (MSP). Seeds were first identified from the intersection of MSP and white matter (WM). These seeds comprised seeds in the corpus callosum as cerebrum seeds, and seeds in the pons as cerebellum seeds. In response to identification of the seeds, graph cuts were performed on the white matter, followed by graph cuts on the brain which included both the white matter and the gray matter. However, it was very problematic to find correct (useful) seeds in the low resolution patient data, and often proper areas were scattered or their positioning represented false connections to other areas.

Accordingly a need exists for enhanced brain tumor and cortex reconstructions. The present disclosure provides these enhanced reconstructions while providing additional benefits.

BRIEF SUMMARY

A fully automatic brain tumor and tumor-aware cortex reconstruction system to improve the healthcare experience with machine intelligence. The disclosed technology receives multi-modal MRI data (T1, T1c, T2, T2-Flair) performs joint reconstruction and visualization of tumors, white matter, and gray matter surfaces automatically.

The steps of the method are summarized as follows. (1) Performing a 3D tumor segmentation and classification if data is sufficient. (2) If existing data is insufficient (e.g., training models not found in the database), then the model is trained on-the-fly for tumor segmentation and classification. (3) Using tumor labels, the system performs a tumor-aware cortex segmentation that is adaptive to the presence of the tumor. (4) Finally, with both cortical and tumor labels, the system reconstructs and visualizes both tumor and cortical surfaces for diagnostic and surgical guidance.

The disclosed technology has been validated by a publicly-available challenge dataset, specifically BraTS2015. A qualitative evaluation indicated that the disclosed method can successfully reconstruct both tumor and cortical surfaces for all relevant datasets.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

DETAILED DESCRIPTION

Figure 1:
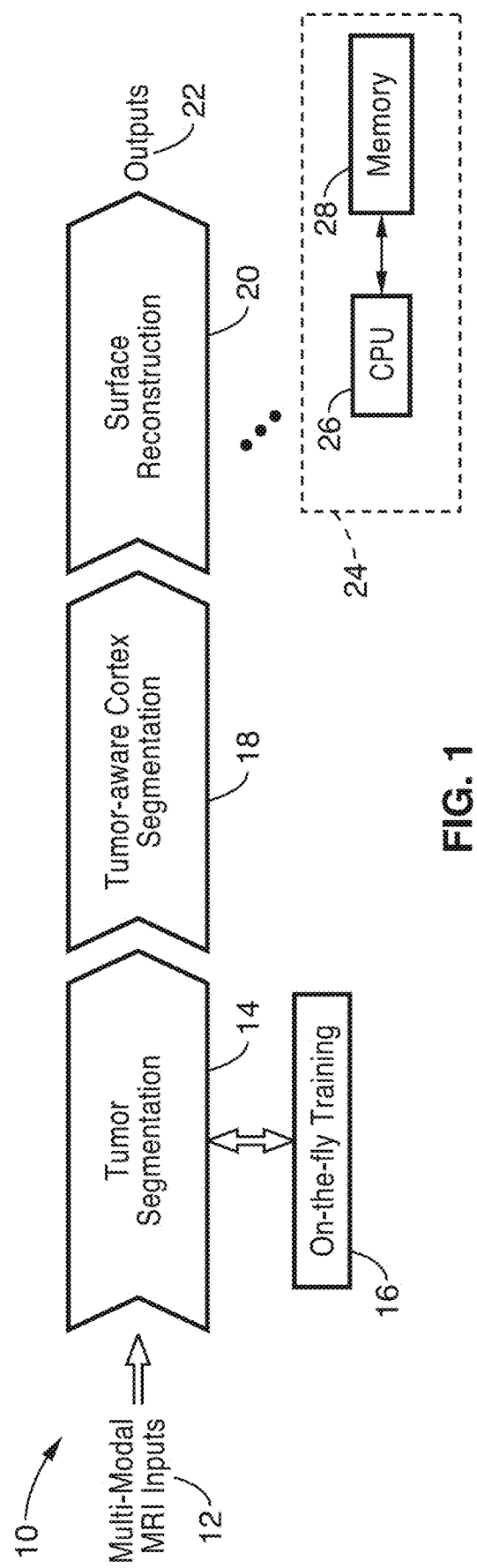
FIG. 1 is a flow diagram for processing steps for joint brain tumor and cortex reconstruction, including on-the-fly training, according to an embodiment of the present disclosure.

FIG. 1 illustrates an overview 10 of joint brain tumor and cortex reconstruction of the present disclosure. Multi-modal inputs (e.g., T1, T1c, T2, and FLAIR) are received 12 from a magnetic resonance imaging (MRI) system, for processing according to the present disclosure. This data is received into tumor segmentation module 14 which is configured for performing on-the-fly training 16. Outputs from tumor segmentation are received in a module 18 for performing tumor-aware cortex segmentation. Outputs from tumor-aware cortex segmentation are received in module 20 for performing surface reconstructions, before generating an output 22 which delineates white matter, grey matter, tumor edema, and a tumor active core.

Processing 24 within each of these modules is shown exemplified with at least one computer (CPU) 26 along with memory 28. It will be appreciated that instructions/programming stored on memory (computer readable media) 28 is executable on computer processor 26. The presented technology is non-limiting with regard to memory and computer-readable media, insofar as these are non-transitory, and thus not constituting a transitory electronic signal.

Figure 2:
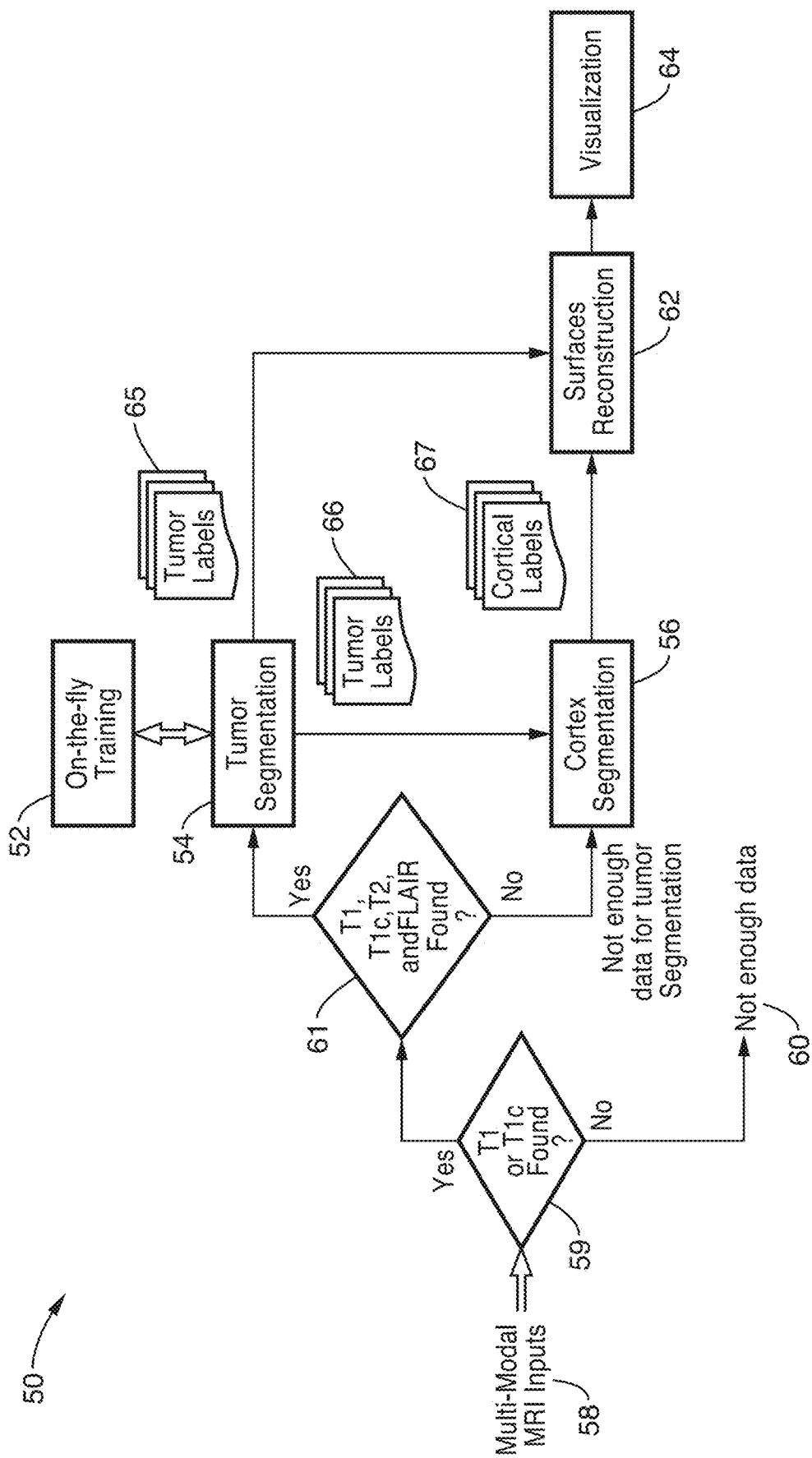
FIG. 2 is a flow diagram for joint brain tumor and cortex reconstruction, shown with MRI input data checking and on-the-fly training, according to an embodiment of the present disclosure.

FIG. 2 illustrates an example embodiment 50 of performing the joint brain tumor and cortex reconstruction for the present disclosure. The technique utilizes on-the-fly training 52 for the tumor segmentation 54 which provides outputs for cortex segmentation 56. In this process, the multi-modal inputs 58 (e.g., T1, T1 c, T2, and FLAIR) are received at block 59 which determines if T1 or T1c inputs were received. If there were no T1 or T1c inputs received, then execution ends at block 60 indicating that insufficient data was received. If at least T1 or T1c were received, then execution moves from block 59 to 61 where a check is made to determine if all the multi-modal inputs of T1, T1 c, T2 and FLAIR were received. If not, then insufficient data for tumor segmentation is available, so that module is bypassed with execution directed to block 56. With sufficient information execution moves from decision 61 to tumor segmentation block 54, which is configured for on-the-fly training 52. In one embodiment, if trained models are available/found, then these models are loaded for segmentation; otherwise a classifier is trained based on training data. Output from tumor segmentation generates tumor labels 65, 66 for use in cortex segmentation and surfaces reconstruction, respectively. It should be appreciated that labels represent multi-class tumor segmentation results, such as to be one of Edema, Non-enhancing Core, Tumor Active and Necrosis Core, they are on every voxel (as in 3D). Results from tumor segmentation are utilized in cortex segmentation 56, whose output is labeled with cortical labels 67. A surfaces reconstruction 62 is performed using inputs from cortex segmentation 56, and preferably tumor segmentation 54 if that data is available. Output with the reconstructed surfaces is received in a visualization block 64 generates the visual attributes for delineating white matter, grey matter, tumor edema, and a tumor active core for use in creating a 3D image presentation.

Figure 3A:
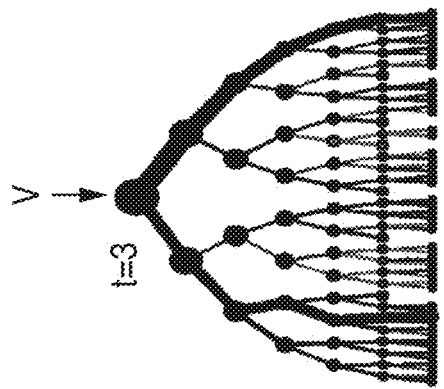
FIG. 3A through FIG. 3F are pairs of tree diagrams and results shown as bar chart probabilities from training models utilized according to an embodiment of the present disclosure.
Figure 3B:
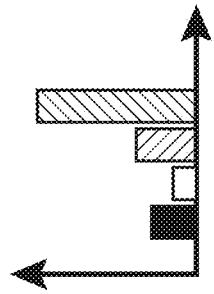
Figure 3C:
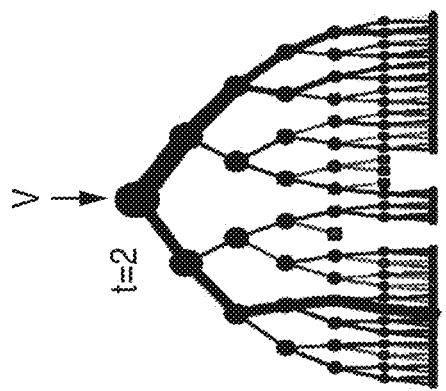
Figure 3D:
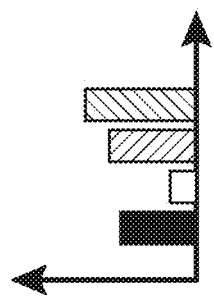
Figure 3E:
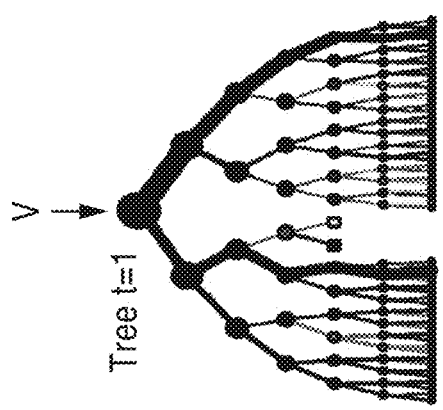
Figure 3F:
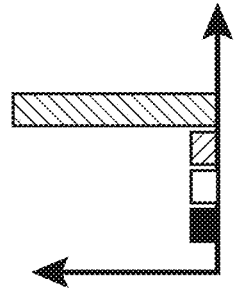

FIG. 3A through FIG. 3F illustrate use of training models for on-the-fly training, which in one embodiment utilizes random forest training, which classifies tumor labels by trained decision trees. By way of example and not limitation, the figures depict three decision tree-result bar graph pairs. Each pair of figures depicts an executed decision tree and the probabilities for each class label. Decisions are made at each node of the tree (FIG. 3A, FIG. 3C, FIG. 3E) based on randomly selected features at the node. The tree, for example, takes the left path if the feature is below or equal to a threshold level, and alternatively takes the right path for a feature value above the threshold. After a series of decisions (these trees show 5 decision levels), a leaf node is reached at which time class label probabilities are available as depicted by the bar graphs (FIG. 3B, FIG. 3D, FIG. 3F). Thus, class labels of the training voxels are reached at the same leaf node and representing tumor class probability. The four bars in these bar charts represent labels for Edema, Non-enhancing Core, Tumor Active, and Necrosis Core. Random forests are composed by a set of decision trees. It should be appreciated that more trees are utilized for estimating the posterior view from different feature combinations to produce a more robust model (e.g., not pruned to overfit the model).

Figure 4:
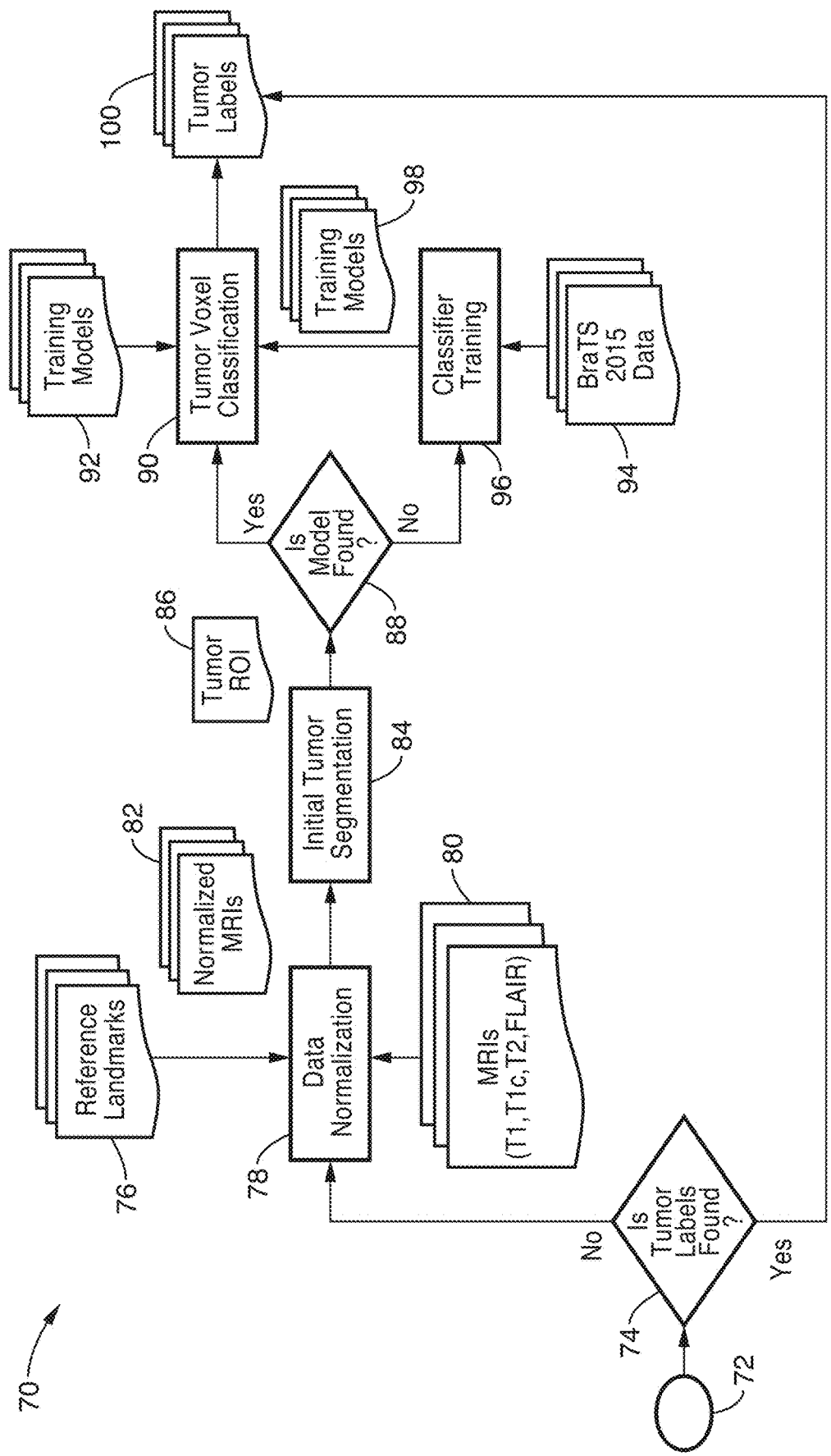
FIG. 4 is a flow diagram for the brain tumor segmentation process according to an embodiment of the present disclosure.

FIG. 4 illustrates an example embodiment 70 of the brain tumor segmentation process. Inputs 72 are checked at block 74 for tumor labels, with execution directed to block 100 if the tumor labels are already present. Otherwise segmentation is performed starting at block 78 with data normalization, which makes use of reference landmarks 76, and data on the multi-modal inputs of the MRI (T1, T1c, T2 and FLAIR). Normalized MRIs 82 are output to initial tumor segmentation block 84, which outputs tumor region(s) of interest (ROI) 86. A check is made 88 if the trained model of a classifier is found. If not, then classifier training is performed 96 using classification data, such as found in MRI datasets, for instance the MICCAI BraTS2015 Dataset. Tumor voxel classification 90 is then performed using either the model information detected at block 88, or from training models 98 received from classifier training 96. Tumor labels 100 are generated from the tumor voxel classification process.

Figure 5:
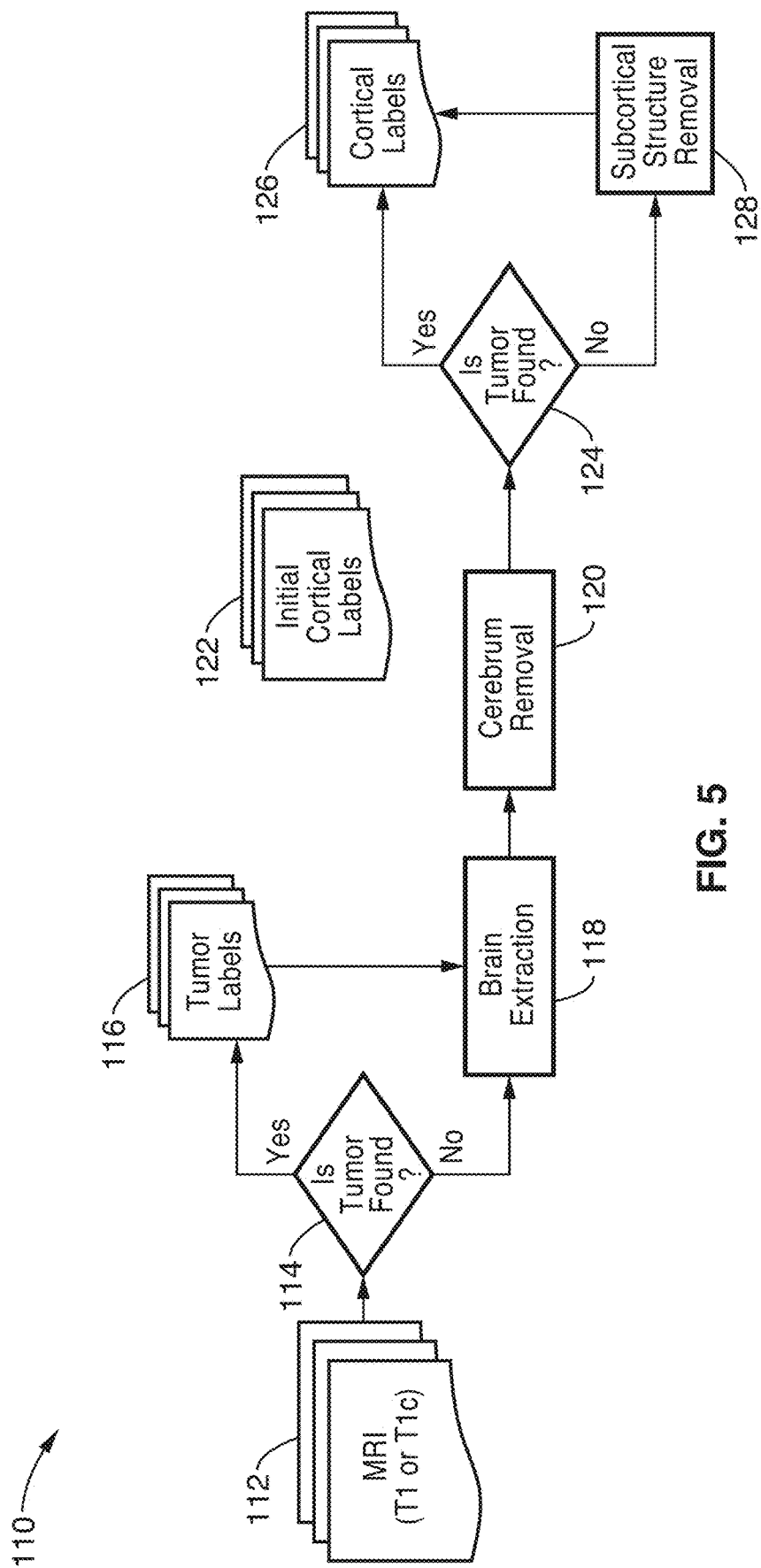
FIG. 5 is a flow diagram for the brain cortex segmentation process according to an embodiment of the present disclosure.

FIG. 5 illustrates an example embodiment 110 of brain cortex segmentation. MRI data (T1 or T1c) is received 112, and a check 114 is made if a tumor was found. If a tumor was found, execution moves to block 116 with tumor labels generated. Otherwise, if no tumor was found, then execution proceeds forward with the brain extraction process 118, whose output is utilized in a cerebrum removal process 120 that outputs initial cortical labels 122. Another level of checks is then performed to determine if the tumor is found 124. If a tumor is found from this data, then cortical labels 126 have been determined. Otherwise, a subcortical structure removal process 128 is integrated for generating cortical labels 126.

Figure 6:
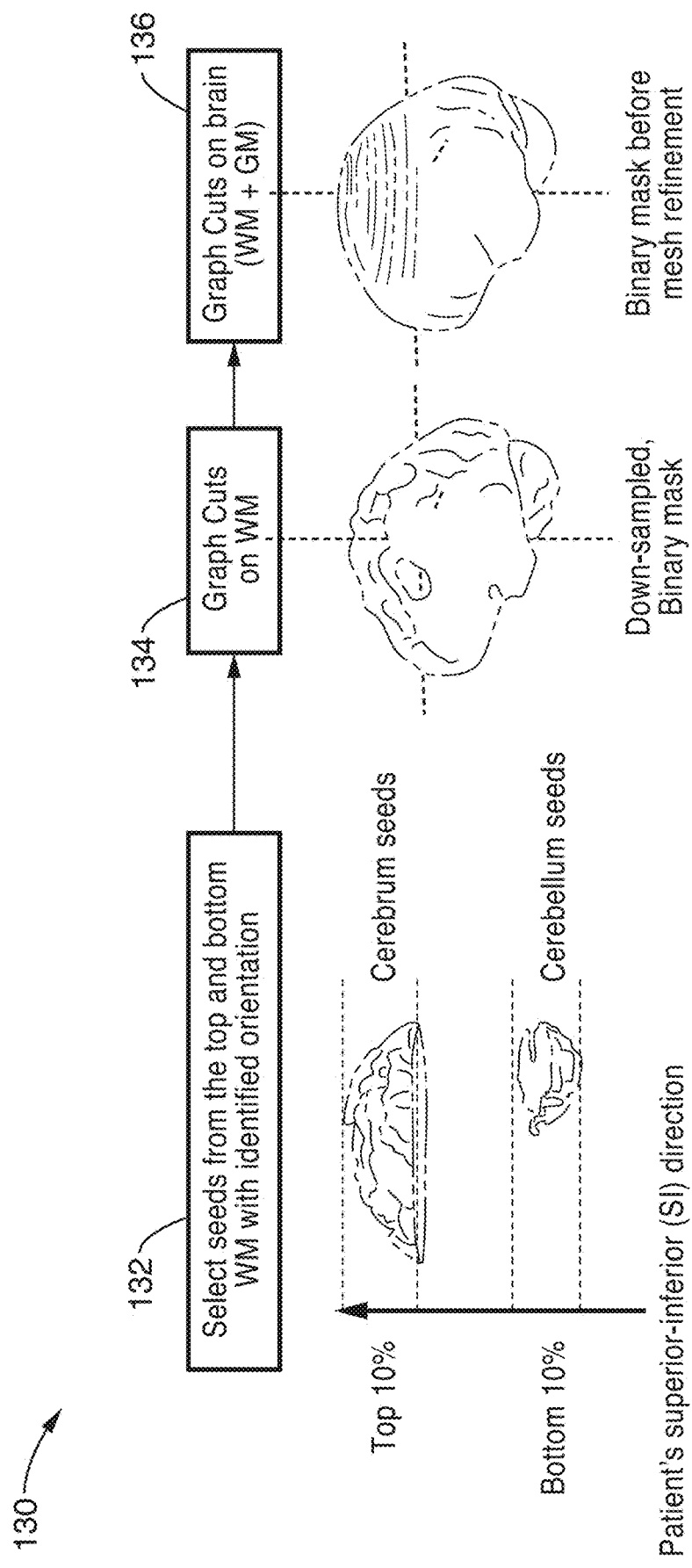
FIG. 6 is a flow diagram of an enhanced process for utilizing seeds and graph cuts according to an embodiment of the present disclosure.

FIG. 6 illustrates an example embodiment 130 of a new approach to the MRI detection and reconstruction process utilizing graph cuts with "simpler" seeds. First seeds are selected 132 from portions of the top and bottom of the WM with identified orientations. For example these seeds may be selected from a top percentage (e.g., 10%) and bottom percentage (e.g., 10%) of the data with respect to the patients superior-inferior (SI) direction. After this graph cuts are performed 134 on a downsampled binary mask. Then the graph cuts are performed 136 on the binary mask for the brain (WM and GM) prior to mesh refinement. This approach provides a simpler way to overcome the deficiency problem with the data sets.

In this simple seeding process, which is based on brain anatomy, the top 10% data surely belongs to the Cerebrum and the bottom 10% data surely belongs to the Cerebellum. Thus, the initial seeds are fairly well known to be accurate. The seeds are utilized as constraints for applying graph cuts to separate the Cerebrum and the Cerebellum by optimizing a cost function. Using this simpler seeding mechanism, the seeds are more readily and accurately found. This seeding process works well even with low-resolution data, from which the more sophisticated structures, such as corpus callosum and pons are difficult to extract.

Figure 7:
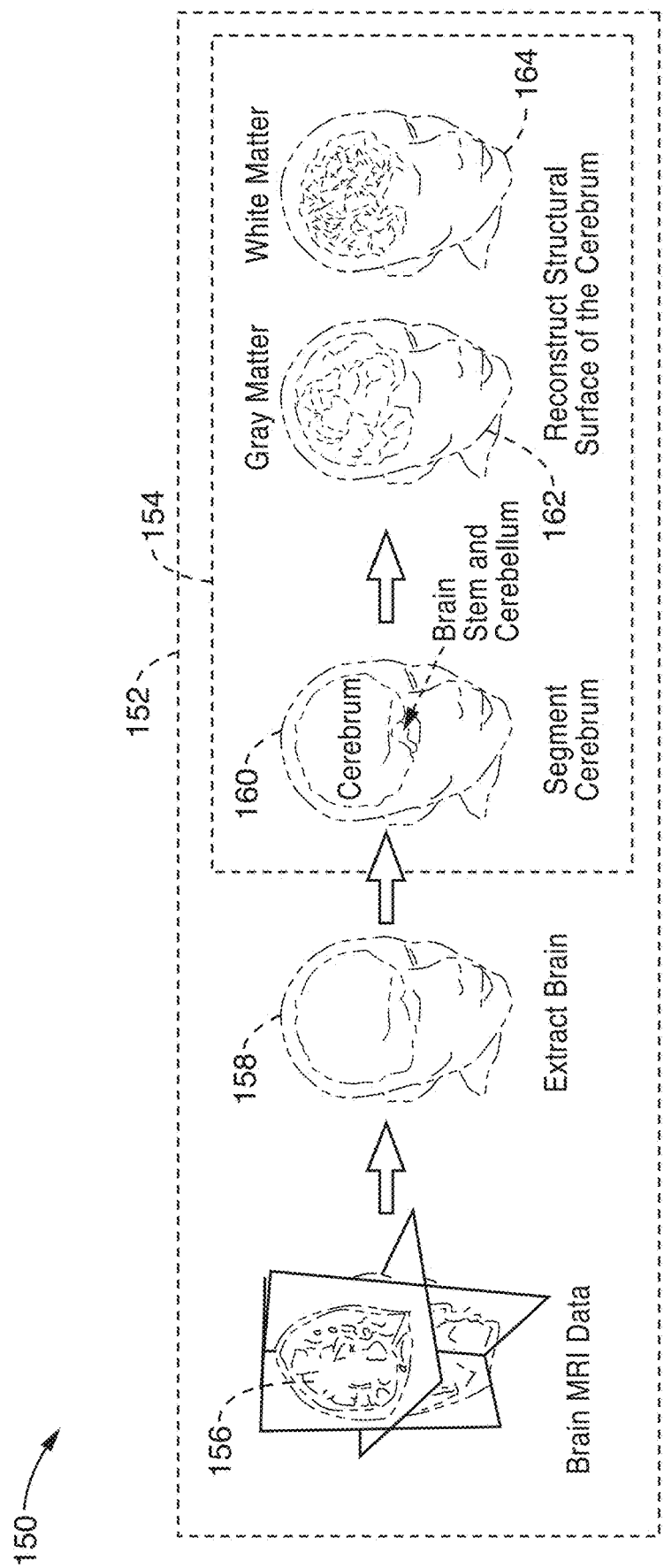
FIG. 7 is a flow diagram of an enhanced refinement process utilized according to an embodiment of the present disclosure.

FIG. 7 illustrates an example embodiment 150 of refinement in the present disclosure, showing the entire process 152 with the refinement outlined 154. In this process, brain MRI data 156 is processed to extract 158 the brain, then the brain stem and cerebellum are segmented 160 from the cerebrum. After this a reconstruction of the structural surfaces of the cerebrum is performed detailing gray matter 162 and white matter 164. In this process a boundary check for segmentation has been added. A simplified mesh post-processing step is utilized. In addition a surface visualization generated showing joint tumor and cortical surfaces.

Figure 8C:
FIG. 8A through FIG. 8C are image renderings showing undesired mesh topology corrections which are overcome according to an embodiment of the present disclosure.
Figure 8A:
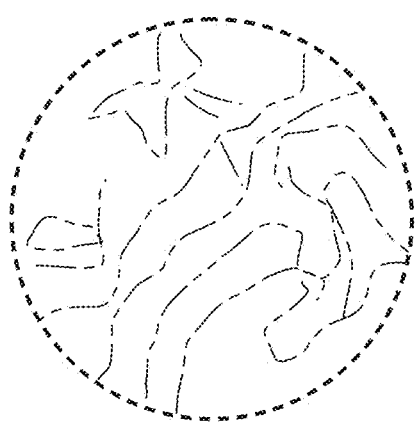
Figure 8B:
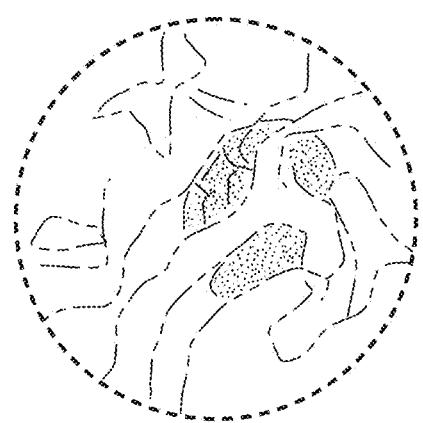

FIG. 8A through FIG. 8C illustrate simplified mesh post processing according to the present disclosure. This processing step eliminates undesired mesh topology corrections which are performed in response to deficient topologies found in tumorous datasets (e.g., BraTS2015). It will be appreciated that use of mesh topologies can over-compensate and create artificial hump in the sulci. FIG. 8A depicts a portion of the topology before correction, with FIG. 8B depicting how conventional mesh correction has filled in some areas with artificial humps. In FIG. 8C a wider view is seen with a large number of these mesh over-corrections showing them in a majority of the sulci. In one embodiment of the present disclosure mesh topology correction is skipped for images in which the presence of a tumor has already been identified. It will be appreciated that other approaches may be utilized, apart from skipping the correction, however these approaches should appreciate that the sphere topology constraint for a normal cortex surface may not be valid in the case of tumorous data.

Figure 9A:
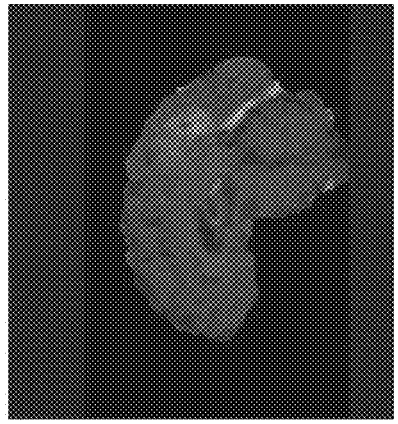
FIG. 9A through FIG. 9C are images of different view data within the MRI data for a given patient, which is received for processing according to an embodiment of the present disclosure.
Figure 9B:
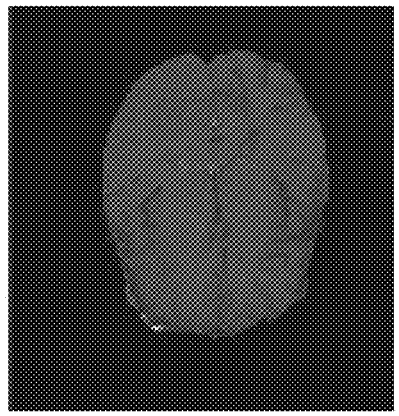
Figure 9C:
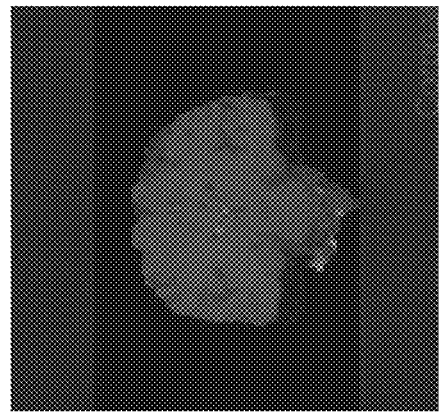
Figure 10B:
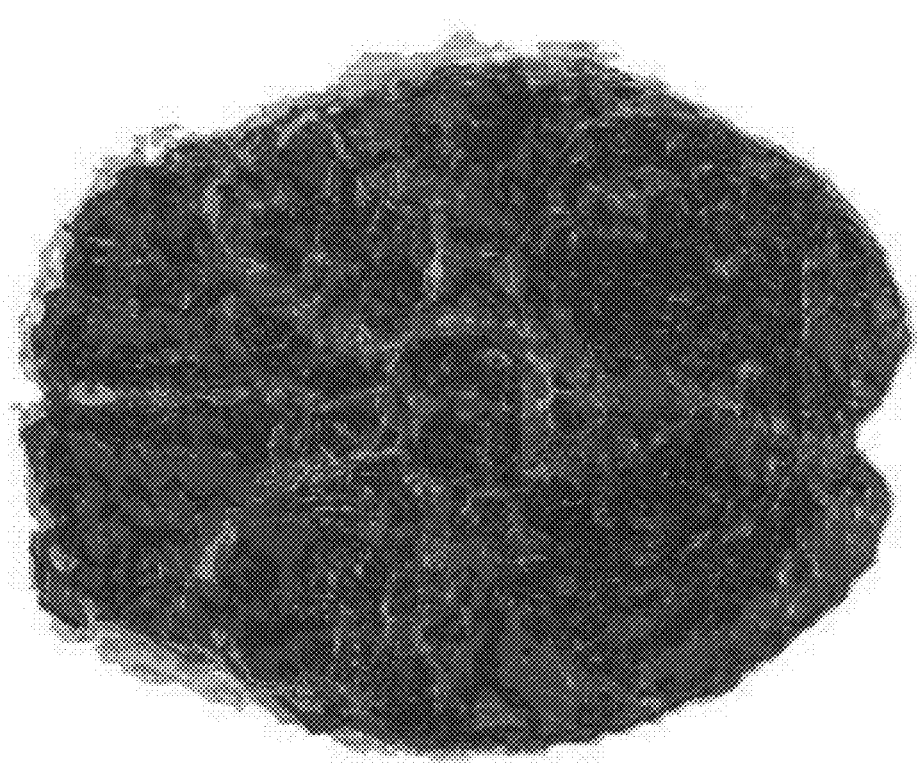
FIG. 10A through FIG. 10D are 2D images output from the joint brain tumor and cortex reconstruction method according to an embodiment of the present disclosure.
Figure 10A:
Figure 10C:
Figure 10D:
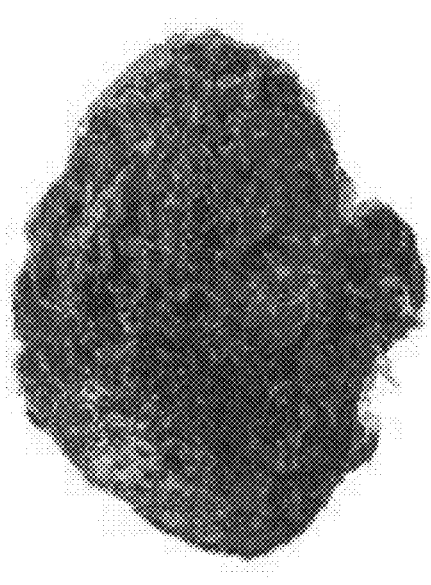

FIG. 9A through FIG. 9C depict axial, sagittal and coronal views, respectively, from the MRI data.

FIG. 10A through FIG. 10D illustrate example output from the present disclosure showing visualizations of tumor and cortical surfaces in the same coordinate space. In particular a view is seen from the top in FIG. 10A, from the bottom in FIG. 10B, from the left in FIG. 10C, and from the right in FIG. 10D. It should be appreciated that the images depicted here in this application are monochrome, while in practice the gray matter, white matter, tumor edema, and tumor active core are shown in different colors (e.g., light grey, dark gray, red and yellow respectively).

The outputs from the method of the present disclosure for joint tumor and surface reconstruction have been systematically validated using the BraTS2015 dataset which contains 274 cases. In these tests only one failure case was found, and this was for a case in which MRI data has an exceedingly low image contrast which is rarely seen in diagnostic scans.

Figure 11:
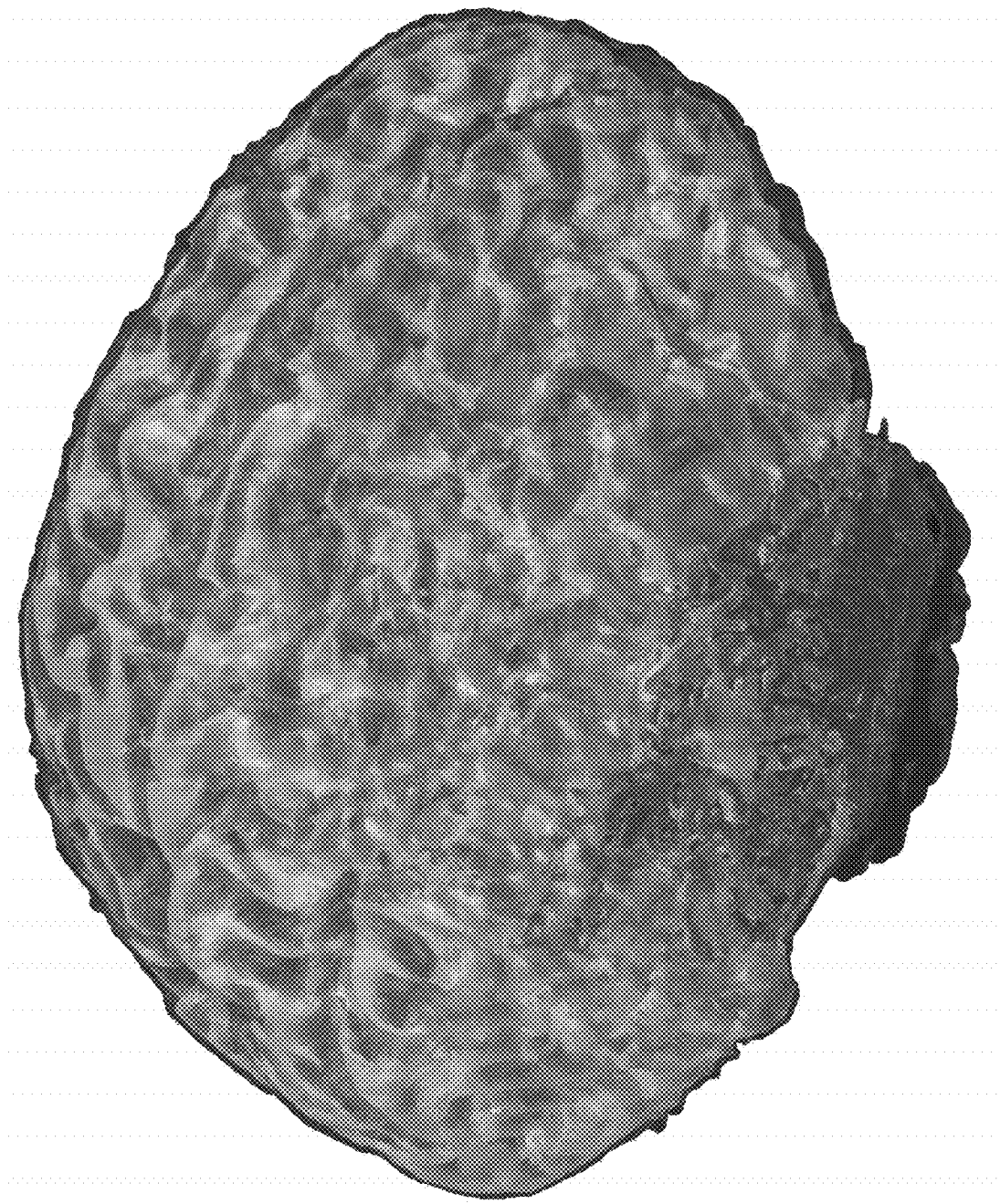
FIG. 11 is a 3D image output from the joint brain tumor and cortex reconstruction method according to an embodiment of the present disclosure.

FIG. 11 illustrates an example output as a 3D image showing the reconstruction with colored delineation of the white matter, gray matter, tumor active area and tumor edema.

The enhancements described in the presented technology can be readily implemented within various MRI image processing apparatus. It should also be appreciated that MRI image processing equipment includes one or more computer processor devices (e.g., CPU, microprocessor, microcontroller, computer enabled ASIC, etc.) and associated memory storing instructions (e.g., RAM, DRAM, NVRAM, FLASH, computer readable media, etc.) whereby programming (instructions) stored in the memory are executed on the processor to perform the steps of the various process methods described herein. The presented technology is non-limiting with regard to memory and computer-readable media, insofar as these are non-transitory, and thus not constituting a transitory electronic signal.

Embodiments of the present technology may be described herein with reference to flowchart illustrations of methods and systems according to embodiments of the technology, and/or procedures, algorithms, steps, operations, formulae, or other computational depictions, which may also be implemented as computer program products. In this regard, each block or step of a flowchart, and combinations of blocks (and/or steps) in a flowchart, as well as any procedure, algorithm, step, operation, formula, or computational depiction can be implemented by various means, such as hardware, firmware, and/or software including one or more computer program instructions embodied in computer-readable program code. As will be appreciated, any such computer program instructions may be executed by one or more computer processors, including without limitation a general purpose computer or special purpose computer, or other programmable processing apparatus to produce a machine, such that the computer program instructions which execute on the computer processor(s) or other programmable processing apparatus create means for implementing the function(s) specified.

Accordingly, blocks of the flowcharts, and procedures, algorithms, steps, operations, formulae, or computational depictions described herein support combinations of means for performing the specified function(s), combinations of steps for performing the specified function(s), and computer program instructions, such as embodied in computer-readable program code logic means, for performing the specified function(s). It will also be understood that each block of the flowchart illustrations, as well as any procedures, algorithms, steps, operations, formulae, or computational depictions and combinations thereof described herein, can be implemented by special purpose hardware-based computer systems which perform the specified function(s) or step(s), or combinations of special purpose hardware and computer-readable program code.

Furthermore, these computer program instructions, such as embodied in computer-readable program code, may also be stored in one or more computer-readable memory or memory devices that can direct a computer processor or other programmable processing apparatus to function in a particular manner, such that the instructions stored in the computer-readable memory or memory devices produce an article of manufacture including instruction means which implement the function specified in the block(s) of the flowchart(s). The computer program instructions may also be executed by a computer processor or other programmable processing apparatus to cause a series of operational steps to be performed on the computer processor or other programmable processing apparatus to produce a computer-implemented process such that the instructions which execute on the computer processor or other programmable processing apparatus provide steps for implementing the functions specified in the block(s) of the flowchart(s), procedure (s) algorithm(s), step(s), operation(s), formula(e), or computational depiction(s).

It will also be appreciated that the terms "programming" or "program executable" as used herein refer to one or more instructions that can be executed by one or more computer processors to perform one or more functions as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors.

It will further be appreciated that as used herein, that the terms processor, computer processor, central processing unit (CPU), and computer are used synonymously to denote a device capable of executing the instructions and communicating with input/output interfaces and/or peripheral devices, and that the terms processor, computer processor, CPU, and computer are intended to encompass single or multiple devices, single core and multicore devices, and variations thereof.

From the description herein, it will be appreciated that the present disclosure encompasses multiple embodiments which include, but are not limited to, the following:

1. An apparatus for performing fully automatic brain tumor and tumor-aware cortex segmentation and reconstruction, comprising: (a) a computer processor; and (b) a non-transitory computer-readable memory storing instructions executable by the computer processor; (c) wherein said instructions, when executed by the computer processor, perform joint reconstruction and visualization of tumors, white matter, and gray matter surfaces automatically with steps comprising: (c)(i) receiving multi-modal MRI data for a case; (c)(ii) performing 3D tumor segmentation and classification if data is sufficient, and training a model on-the-fly for tumor segmentation and classification if existing data is insufficient; (c)(iii) performing a tumor-aware cortex segmentation utilizing tumor labels and adapting to presence of a tumor; and (c)(iv) reconstructing and visualizing both tumor and cortical surfaces utilizing both cortical and tumor labels to output images that provide diagnostic and surgical guidance in discerning between gray matter, white matter, tumor edema, and tumor active core regions.

2. The apparatus of any preceding embodiment, wherein said MRI data comprises T1, T1c, T2, and T2-Flair data.

3. The apparatus of any preceding embodiment, wherein said instructions when executed by the computer processor further comprise adjusting processing of said MRI data based on which modes of multi-modal MRI data is received.

4. The apparatus of any preceding embodiment, wherein said instructions when executed by the computer processor are configured for performing said training a model on-the-fly by utilizing random forest training for classifying tumor labels by using trained decision trees.

5. The apparatus of any preceding embodiment, wherein said instructions when executed by the computer processor further comprise performing segmentation and reconstructions utilizing graph cuts determined from simple seeds, in which said simple seeds are selected from a top and bottom percentage of the data with respect to patient superior-inferior direction.

6. The apparatus of any preceding embodiment, wherein said instructions when executed by the computer processor further comprise first performing said graph cuts on a downsampled binary mask.

7. The apparatus of any preceding embodiment, wherein said instructions when executed by the computer processor further comprise performing a simplified mesh post processing step which eliminates undesired mesh topology corrections performed in response to deficient topologies in a tumerous dataset.

8. The apparatus of any preceding embodiment, wherein said instructions when executed by the computer processor further comprise skipping said mesh topology correction for images in which the presence of a tumor has already been identified.

9. The apparatus of any preceding embodiment, wherein said instructions when executed by the computer processor further comprise taking into account deformed anatomy which arises in response to a tumor.

10. An apparatus for performing fully automatic brain tumor and tumor-aware cortex segmentation and reconstruction, comprising: (a) a computer processor; and (b) a non-transitory computer-readable memory storing instructions executable by the computer processor; (c) wherein said instructions, when executed by the computer processor, perform joint reconstruction and visualization of tumors, white matter, and gray matter surfaces automatically with steps comprising: (c)(i) receiving multi-modal MRI data, comprising T1, T1c, T2, and T2-Flair data for a patient; (c)(ii) performing 3D tumor segmentation and classification if data is sufficient, and training a model on-the-fly for tumor segmentation and classification if existing data is insufficient; (c)(iii) utilizing random forest training for classifying tumor labels by using trained decision trees when training a model on-the-fly; (c)(iv) performing a tumor-aware cortex segmentation utilizing tumor labels and adapting to presence of a tumor; and (c)(v) reconstructing and visualizing both tumor and cortical surfaces utilizing both cortical and tumor labels to output images that provide diagnostic and surgical guidance in discerning between gray matter, white matter, tumor edema, and tumor active core regions.

11. The apparatus of any preceding embodiment, wherein said instructions when executed by the computer processor further comprise adjusting processing of said MRI data based on which modes of multi-modal MRI data is received.

12. The apparatus of any preceding embodiment, wherein said instructions when executed by the computer processor are configured for performing said training a model on-thefly by utilizing random forest training for classifying tumor labels by using trained decision trees.

13. The apparatus of any preceding embodiment, wherein said instructions when executed by the computer processor further comprise performing segmentation and reconstructions utilizing graph cuts determined from simple seeds, in which said simple seeds are selected from a top and bottom percentage of the data with respect to patient superior-inferior direction.

14. The apparatus of any preceding embodiment, wherein said instructions when executed by the computer processor further comprise first performing said graph cuts on a downsampled binary mask.

15. The apparatus of any preceding embodiment, wherein said instructions when executed by the computer processor further comprise performing a simplified mesh post processing step which eliminates undesired mesh topology corrections performed in response to deficient topologies in a tumerous dataset.

16. The apparatus of any preceding embodiment, wherein said instructions when executed by the computer processor further comprise skipping said mesh topology correction for images in which the presence of a tumor has already been identified.

17. The apparatus of any preceding embodiment, wherein said instructions when executed by the computer processor further comprise taking into account deformed anatomy which arises in response to a tumor.

18. A method of performing fully automatic brain tumor and tumor-aware cortex segmentation and reconstruction, by steps comprising: (a) receiving multi-modal MRI data, which may include T1, T1c, T2, and T2-Flair data, in an electronic device for imaging MRI data to perform joint reconstruction and visualization of tumors, white matter, and gray matter surfaces automatically; (b) performing 3D tumor segmentation and classification if data is sufficient, and training a model on-the-fly for tumor segmentation and classification if existing data is insufficient; (c) performing a tumor-aware cortex segmentation utilizing tumor labels and adapting to presence of a tumor; and (d) reconstructing and visualizing both tumor and cortical surfaces utilizing both cortical and tumor labels to output images that provide diagnostic and surgical guidance in discerning between gray matter, white matter, tumor edema, and tumor active core regions.

19. The method of any preceding embodiment, further comprising adjusting processing of said MRI data based on which modes of multi-modal MRI data is received.

20. The method of any preceding embodiment, wherein said training a model on-the-fly is performed by utilizing random forest training for classifying tumor labels by using trained decision trees.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. An apparatus for performing fully automatic brain tumor and tumor-aware cortex segmentation and reconstruction, comprising:
    (a) a computer processor; and
    (b) a non-transitory computer-readable memory storing instructions executable by the computer processor;
    (c) wherein said instructions, when executed by the computer processor, perform brain tumor and tumor-aware cortex segmentation and reconstruction using joint reconstruction and visualization of tumors, white matter, and gray matter surfaces automatically with steps comprising:
        (i) receiving multi-modal magnetic resonance image (MRI) data for a case;
        (ii) determining whether received multi-modal MRI data has sufficient inputs and reference landmarks;
        (iii) normalizing multi-modal MRI data determined to have sufficient inputs and performing 3D tumor segmentation with reference landmarks and data on multi-modal inputs of the MRI, and classification;
        (iv) training a model on-the-fly for tumor 3D segmentation and classification if existing data is determined to be insufficient;
        (v) performing a cortex segmentation using outputs from said tumor segmentation creating a tumor-aware cortex segmentation, wherein said tumor-aware cortex segmentation is configured to generate tumor labels which represent multi-class tumor segmentation results selected from a group of results consisting of Edema, Non-enhancing Core, Tumor Active and Necrosis Core, for ever voxel, and adapting to a presence of a tumor; and
        (vi) reconstructing and visualizing both tumor and cortical surfaces utilizing both cortical and tumor labels to output images that provide diagnostic and surgical guidance in discerning between gray matter, white matter, tumor edema, and tumor active core regions.

2. The apparatus as recited in claim 1, wherein said multi-modal MRI data comprises T1, T1c, T2, and T2-Flair data.

3. The apparatus as recited in claim 1, wherein said instructions when executed by the computer processor further comprise adjusting processing of said MRI data based on which modes of multi-modal MRI data are received.

4. The apparatus as recited in claim 1, wherein said instructions when executed by the computer processor are configured for performing said training a model on-the-fly by utilizing random forest training for classifying tumor labels by using trained decision trees.

5. The apparatus as recited in claim 1, wherein said instructions when executed by the computer processor further comprise performing segmentation and reconstructions utilizing graph cuts determined from simple seeds, in which said simple seeds are selected from a top and bottom percentage of the data with respect to patient superior-inferior direction.

6. The apparatus as recited in claim 5, wherein said instructions when executed by the computer processor further comprise first performing said graph cuts on a down-sampled binary mask.

7. The apparatus as recited in claim 1, wherein said instructions when executed by the computer processor further comprise performing a simplified mesh post processing step which eliminates undesired mesh topology corrections performed in response to deficient topologies in a tumerous dataset.

8. The apparatus as recited in claim 7, wherein said instructions when executed by the computer processor further comprise skipping said mesh topology correction for images in which the presence of a tumor has already been identified.

9. The apparatus as recited in claim 1, wherein said instructions when executed by the computer processor further comprise taking into account deformed anatomy which arises in response to a tumor.

10. An apparatus for performing fully automatic brain tumor and tumor-aware cortex segmentation and reconstruction, comprising:
 (a) a computer processor; and
 (b) a non-transitory computer-readable memory storing instructions executable by the computer processor;
 (c) wherein said instructions, when executed by the computer processor, perform brain tumor and tumor-aware cortex segmentation and reconstruction using joint reconstruction and visualization of tumors, white matter, and gray matter surfaces automatically with steps comprising:
  (i) determining that multi-modal magnetic resonance image (MRI) data, comprising T1, T1c, T2, and T2-Flair data have been received for a patient;
  (ii) performing 3D tumor segmentation with data normalization which makes use of reference landmarks and data on multi-modal inputs of the MRI, and uses classification if data is sufficient, and training a model on-the-fly for tumor segmentation and classification if existing data is insufficient;
  (iii) utilizing random forest training for classifying tumor labels by using trained decision trees when training a model on-the-fly;
  (iv) performing a tumor-aware cortex segmentation, using outputs from said tumor segmentation, which is configured to generate tumor labels which represent multi-class tumor segmentation results selected from a group of results consisting of Edema, Non-enhancing Core, Tumor Active and Necrosis Core, for every voxel, and adapting to presence of a tumor; and
  (v) reconstructing and visualizing both tumor and cortical surfaces utilizing bath cortical and tumor labels to output images that provide diagnostic and surgical guidance in discerning between gray matter, white matter, tumor edema, and tumor active core regions.

11. The apparatus as recited in claim 10, wherein said instructions when executed by the computer processor further comprise adjusting processing of said MRI data based on which modes of multi-modal MRI data is received.

12. The apparatus as recited in claim 10, wherein said instructions when executed by the computer processor are configured for performing said training a model on-the-fly by utilizing random forest training for classifying tumor labels by using trained decision trees.

13. The apparatus as recited in claim 10, wherein said instructions when executed by the computer processor further comprise performing segmentation and reconstructions utilizing graph cuts determined from simple seeds, in which said simple seeds are selected from a top and bottom percentage of the data with respect to patient superior-inferior direction.

14. The apparatus as recited in claim 13, wherein said instructions when executed by the computer processor further comprise first performing said graph cuts on a down-sampled binary mask.

15. The apparatus as recited in claim 10, wherein said instructions when executed by the computer processor further comprise performing a simplified mesh post processing step which eliminates undesired mesh topology corrections performed in response to deficient topologies in a tumerous dataset.

16. The apparatus as recited in claim 15, wherein said instructions when executed by the computer processor further comprise skipping said mesh topology correction for images in which the presence of a tumor has already been identified.

17. The apparatus as recited in claim 10, wherein said instructions when executed by the computer processor further comprise taking into account deformed anatomy which arises in response to a tumor.

18. A method of performing fully automatic brain tumor and tumor-aware cortex segmentation and reconstruction, by steps comprising:
 (a) receiving multi-modal magnetic resonance image (MRI) data, which may include T1, T1c, T2, and T2-Flair data, in an electronic device for imaging MRI data to perform joint reconstruction and visualization of tumors, white matter, and gray matter surfaces automatically;
 (b) performing 3D tumor segmentation with data normalization which makes use of reference landmarks and data on multi-modal inputs of the MRI, and uses classification if data is sufficient, and training a model on-the-fly for tumor segmentation and classification if existing data is insufficient;
 (c) determining that multi-modal inputs T1, T1c, T2 and FLAIR are received and performing tumor segmentation comprising (A) determining that a trained model of a classifier is not found; and (B) performing classifier training using on-the-fly random forest training;
 (d) performing a tumor-aware cortex segmentation using outputs from said tumor segmentation, wherein said tumor-aware cortex segmentation is configured to generate tumor labels which represent multi-class tumor segmentation results selected from a group of results consisting of Edema, Non-enhancing Core, Tumor Active and Necrosis Core, for every voxel, and adapting to presence of a tumor; and
 (e) reconstructing and visualizing both tumor and cortical surfaces utilizing both cortical and tumor labels to output images that provide diagnostic and surgical guidance in discerning between gray matter, white matter, tumor edema, and tumor active core regions to provide brain tumor and tumor-aware cortex segmentation and reconstruction.

19. The method as recited in claim 18, further comprising adjusting processing of said MRI data based on which modes of multi-modal MRI data is received.

20. The method as recited in claim 18, wherein said training a model on-the-fly is performed by utilizing random forest training for classifying tumor labels by using trained decision trees.

* * * * *